(12) United States Patent
Fisher et al.

(10) Patent No.: US 8,267,370 B2
(45) Date of Patent: Sep. 18, 2012

(54) CLAMP FOR FLEXIBLE TUBING

(75) Inventors: Mark S. Fisher, Sellersville, PA (US); W. Shaun Wall, North Wales, PA (US)

(73) Assignee: Medical Components, Inc., Harleysville, PA (US)

( * ) Notice: Subject to any disclaimer, the term of this patent is extended or adjusted under 35 U.S.C. 154(b) by 366 days.

(21) Appl. No.: 12/607,441

(22) Filed: Oct. 28, 2009

(65) Prior Publication Data

US 2010/0106101 A1    Apr. 29, 2010

Related U.S. Application Data

(60) Provisional application No. 61/108,940, filed on Oct. 28, 2008.

(51) Int. Cl.
*F16K 7/04* (2006.01)
*A61M 5/00* (2006.01)

(52) U.S. Cl. .......................... 251/7; 604/250

(58) Field of Classification Search .............. 251/4, 7, 251/8; 604/34, 250
See application file for complete search history.

(56) References Cited

U.S. PATENT DOCUMENTS

| | | | |
|---|---|---|---|
| 3,942,228 A | 3/1976 | Buckman et al. | |
| 4,106,508 A * | 8/1978 | Berlin | 251/7 |
| 4,235,412 A | 11/1980 | Rath et al. | |
| 4,247,076 A * | 1/1981 | Larkin | 251/7 |
| 4,266,751 A | 5/1981 | Akhavi | |
| 4,326,518 A | 4/1982 | Williams | |
| 4,434,963 A | 3/1984 | Russell | |
| 4,534,089 A | 8/1985 | Swan | |
| 4,560,378 A | 12/1985 | Weiland | |
| 4,586,691 A | 5/1986 | Kozlow | |
| 4,588,160 A | 5/1986 | Flynn et al. | |
| 4,589,626 A | 5/1986 | Kurtz et al. | |
| 4,623,102 A | 11/1986 | Hough, Jr. | |
| 4,634,421 A | 1/1987 | Hegemann | |

(Continued)

FOREIGN PATENT DOCUMENTS

FR    1494814    9/1967

OTHER PUBLICATIONS

International Preliminary Report on Patentability dated Apr. 28, 2011 of PCT Application No. PCT/US09/62311 (6 pages).

(Continued)

*Primary Examiner* — Eric Keasel
(74) *Attorney, Agent, or Firm* — Glenn M. Massina; Fox Rothschild LLP

(57) ABSTRACT

A clamp assembly (10,110) for flexible tubing (100), having a housing (12,112) and a clamp (14,114) slidable within the housing between first and second positions, to occlude the tubing when the clamp is in the second position. Both the clamp and the housing include tubing-engaging ribs (30,60; 130,160) to compress the tubing when the clamp is moved from its first or open position to its second or occluding position, with the tubing-engaging ribs being axially offset to force the tubing (100) into a tortuous path causing occlusion thereof. A pair of latch arms (62) extend forwardly from the clamp to follow respective channels (32) formed into housing side walls (20,22), with latch arm free ends (64) extending beyond the end of the housing to become latchingly engaged therewith when the clamp is moved into its occluding position, and also to be exposed to be manually engaged for delatching when desired.

17 Claims, 16 Drawing Sheets

U.S. PATENT DOCUMENTS

| | | |
|---|---|---|
| 4,643,389 A | 2/1987 | Elson et al. |
| 4,673,161 A | 6/1987 | Flynn et al. |
| 4,736,925 A * | 4/1988 | Kamstrup-Larsen et al. .. 251/10 |
| 4,802,650 A | 2/1989 | Stricker |
| 4,889,527 A | 12/1989 | Herrli |
| RE33,219 E * | 5/1990 | Daniell et al. ............. 251/7 |
| 4,950,255 A | 8/1990 | Brown et al. |
| 4,960,259 A * | 10/1990 | Sunnanvader et al. ......... 251/7 |
| 5,035,399 A | 7/1991 | Rantanen-Lee |
| 5,203,056 A | 4/1993 | Funk et al. |
| 5,238,218 A | 8/1993 | Mackal |
| 5,396,925 A | 3/1995 | Poli |
| 5,429,616 A | 7/1995 | Schaffer |
| 5,549,657 A | 8/1996 | Stern et al. |
| 5,749,859 A | 5/1998 | Powell |
| 5,921,968 A | 7/1999 | Lampropoulos et al. |
| 6,089,527 A | 7/2000 | Utterberg |
| 6,213,988 B1 | 4/2001 | McIvor et al. |
| 6,482,180 B2 | 11/2002 | Toyokawa et al. |
| 6,770,057 B2 * | 8/2004 | Feliciano ............... 604/250 |
| 6,823,617 B2 | 11/2004 | Schweikert |
| 7,329,248 B2 | 2/2008 | Raulerson et al. |
| 7,344,527 B2 | 3/2008 | Schweikert et al. |
| 7,434,779 B2 * | 10/2008 | Werth ................. 251/10 |
| 2004/0089828 A1 | 5/2004 | Werth |
| 2006/0129110 A1 | 6/2006 | Smith et al. |
| 2006/0169934 A1 | 8/2006 | Werth |
| 2007/0261214 A1 | 11/2007 | Nerbonne et al. |
| 2008/0319421 A1 | 12/2008 | Bizup et al. |

OTHER PUBLICATIONS

International Search Report dated, Mar. 1, 2010, PCT/US2009/062311 (5 pages).

Written Opinion dated Mar. 1, 2010, PT/US2009/062311 (5 pages).

* cited by examiner

CLAMP FOR FLEXIBLE TUBING

CROSS-REFERENCE TO RELATED APPLICATIONS

This application claims the benefit of U.S. Provisional Patent Application Ser. No. 61/108,940 filed Oct. 28, 2008.

FIELD OF THE INVENTION

This relates to the field of medical devices and more particularly to flexible medical tubing and clamping thereof.

BACKGROUND OF THE INVENTION

Catheters may be located in various venous locations and cavities throughout the body of a patient for introduction of fluids to a body or removal of fluids from the body. Such catheterization may be performed by using a single catheter having multiple lumens. A typical example of a multiple lumen catheter is a dual lumen catheter assembly in which one lumen introduces fluid and the other lumen removes fluid. Catheterization may also be performed by using multiple single-lumen catheters, such as TESIO® catheters sold by Medical Components, Inc. of Harleysville, Pa.

Each catheter lumen is typically connected to a distal end of an extension tube via a hub permanently secured to the catheter and the distal ends of the extension tubes. Each extension tube has a standard connector, such as a luer fitting, at its proximal end for connection to a medical device, such as a hemodialysis machine. A clamp, such as a Halkey Roberts clamp, is typically disposed over the extension tube. The clamp restricts fluid flow through the extension tube by compressing and closing the extension tube between a pair of clamp jaws. For long term catheterization, the clamp must be opened and closed numerous times, which may lead to a failure of the extension tube and blood loss from the catheter.

Clamps of the basic Halkey Roberts type are well-known, and are disclosed in various patents such as U.S. Pat. Nos. 3,942,228; 4,560,378; 4,588,160; 4,589,626; 5,035,399; 5,203,056; and 6,089,527. Structurally, such a clamp is a one-piece plastic member defined more or less by a skeletal framework and having two transverse end walls with apertures therethrough through which the tubing extends, whereby the clamp self-retains on the tubing even in the unlatched or open position. A latch arm extends from one end wall toward the other and includes a latching structure, and the other end wall includes a catch engageable with the latching structure. The latch arm and an opposing wall to the latch arm include tubing engaging surfaces, or clamp jaws, that engage and compress the tubing when the latch arm is in the latched position, which occludes the tubing to shut off fluid flow through the tubing until the clamp is released.

The end wall of the clamp thus described extends to a free end that is exposed and thus may become easily snagged by foreign objects such as clothing or wires or the like, resulting in unintentional and undesirable delatching and unclamping from the tubing. Also, the tubing's resistance to being clamped exerts force in a direction tending to pry the latch arm to overcome the catch and thus open inadvertently, and the skeletal end wall that is remote from the latching arrangement becomes stressed and weakened over repeated clamping/unclamping cycles, eventually leading to failure and breakage in many cases. Commercially available Halkey Roberts clamps commonly extend along the tubing for a length of just under one inch (254 mm).

In above-cited U.S. Pat. Nos. 4,588,160; 4,589,626; and 4,673,161, the clamping jaws are axially offset. In another patent, U.S. Pat. No. 4,623,102, a clamp is disposed transversely and provides a pair of planar clamping surfaces to grip the tube. In both U.S. Pat. Nos. 4,589,626 and 4,623,102, the clamp has two or more clamping positions, enabling either selective occlusion or capability of utility with tubing of different diameters.

It would be desirable to provide a clamp that is more resistant to delatching, that is more durable and that extends substantially less than one inch along the tubing.

BRIEF SUMMARY OF THE INVENTION

Briefly, the present invention is a clamp assembly for flexible tubing that includes a housing and a clamp that is slidable within the housing between a first, or open, position and a second, or closed, position, wherein when in the second position the tubing is occluded. The housing includes openings in two opposing side walls thereof through which the tubing extends, so that the clamp assembly is oriented, and the clamp is movable, transversely with respect to the tubing and can occupy much less length of the tubing. One of the housing and clamp includes at least a pair of tubing-engaging ribs that engage and compress the tubing against a surface of the other of the housing and clamp, to occlude the tubing when the clamp has been moved to its second position. Preferably, the other of the housing and clamp also includes at least one tubing-engaging rib that compresses the tubing in cooperation with the tubing-engaging ribs of the other when the clamp is in its second position.

Preferably, the clamp includes a pair of latch arms that extend longitudinally from an end thereof through the housing to latch with catches of the housing at a corresponding end thereof when the clamp has been moved to its second position. The tubing when clamped exerts resistance against the ribs of the clamp assembly in a direction transverse to the tubing's axis. The clamping resistance is perpendicular to the deflection direction of the latch arms, thus having an insignificant effect on the latching arrangement. Furthermore, any incidental engagement of the tubing with the latch arms would tend to press the latch arms outwardly against the interior side wall surfaces of the housing, preventing deflection of the latch arms, all of which enables the clamp assembly of the present invention to have superior resistance to inadvertent unclamping and to be more durable and robust over repeated clamping cycles.

Also, preferably, the clamp includes a pair of detents that cooperate with recesses of the housing to secure the clamp in an assembled state with the housing when the clamp is in its first or open position, thus securing the clamp assembly to the flexible tubing. In one embodiment, the pair of detents comprises the latch arm free ends, and the recesses comprise a pair of slots spaced from the second end into which the latch arm free ends snap when the clamp is in its first or open position.

Another embodiment of clamp assembly has an oblate or ovate or ovoid shape that is distinctly atraumatic to the patient. In this embodiment, the assembly comprises a pair of clamping members wherein each member defines a portion of the channel along which the flexible tubing extends, and thus can be applied to the tubing from laterally thereof rather than require insertion through a housing aperture of an end of the tubing, as in the first embodiment, and can, if desired, be easily removable therefrom.

The clamp assembly of the present invention has a more robust structure that is far less likely to be delatched and unclamp the tubing, and less likely to be breakable after repeated usage, and occupies much less length of the tubing.

BRIEF DESCRIPTION OF THE DRAWINGS

The accompanying drawings, which are incorporated herein and constitute part of this specification, illustrate the presently preferred embodiment of the invention, and, together with the general description given above and the detailed description given below, serve to explain the features of the invention. In the drawings.

DETAILED DESCRIPTION OF THE INVENTION

Figure 12:
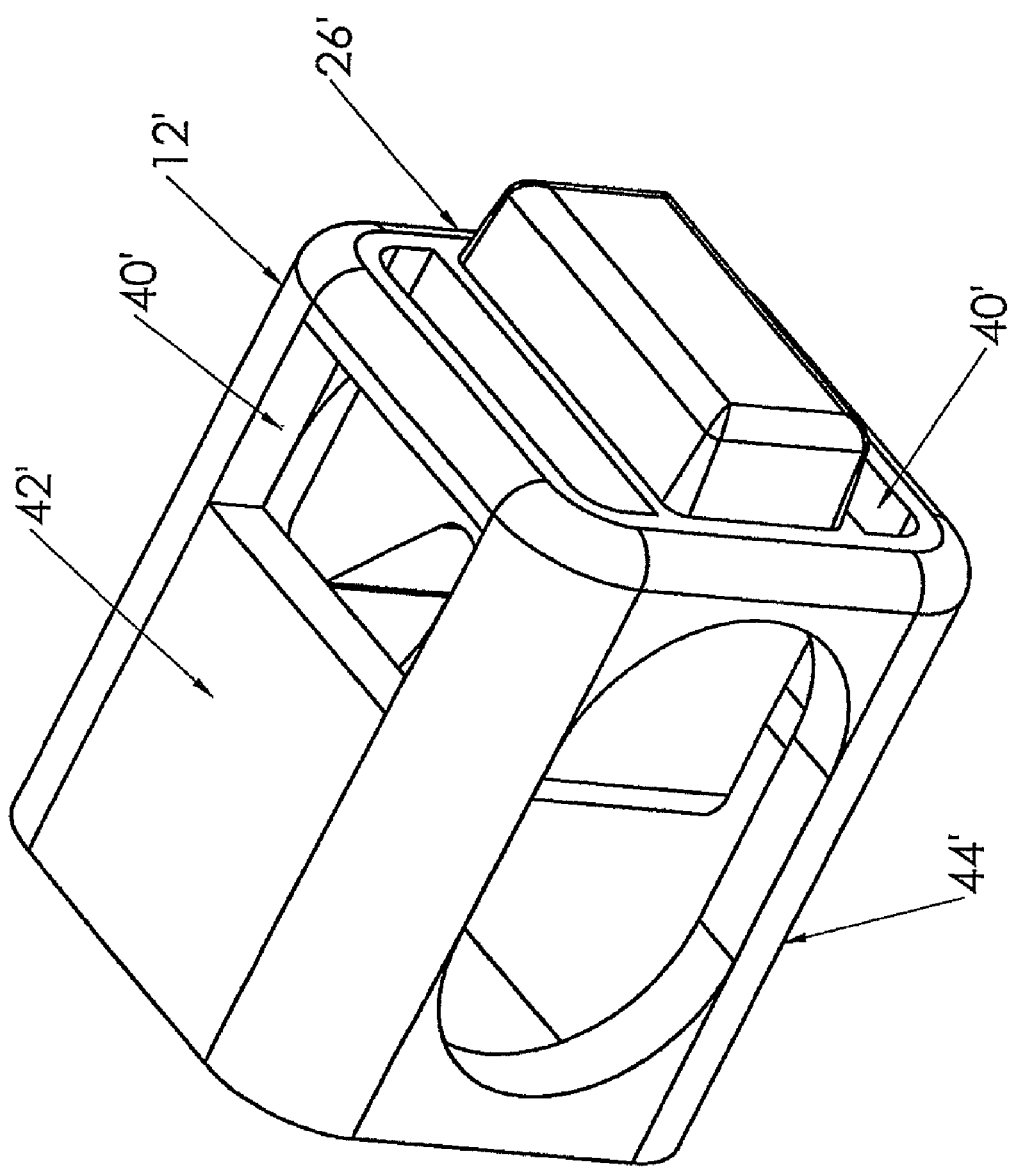
FIG. 12 is an isometric view of an alternate embodiment of housing defining first latching positions of the clamp latch arms when the assembly is in its open position.
Figure 13:
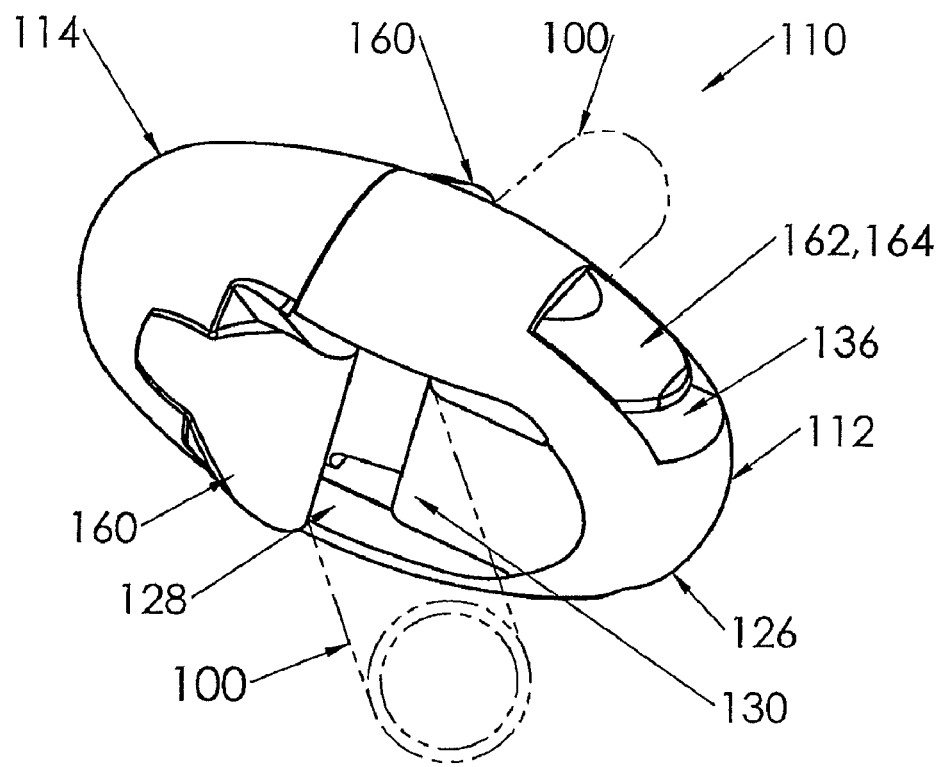
FIGS. 13 and 14 are isometric views of a third embodiment of clamp assembly, with tubing shown in dashed lines clamped thereby.
Figure 14:
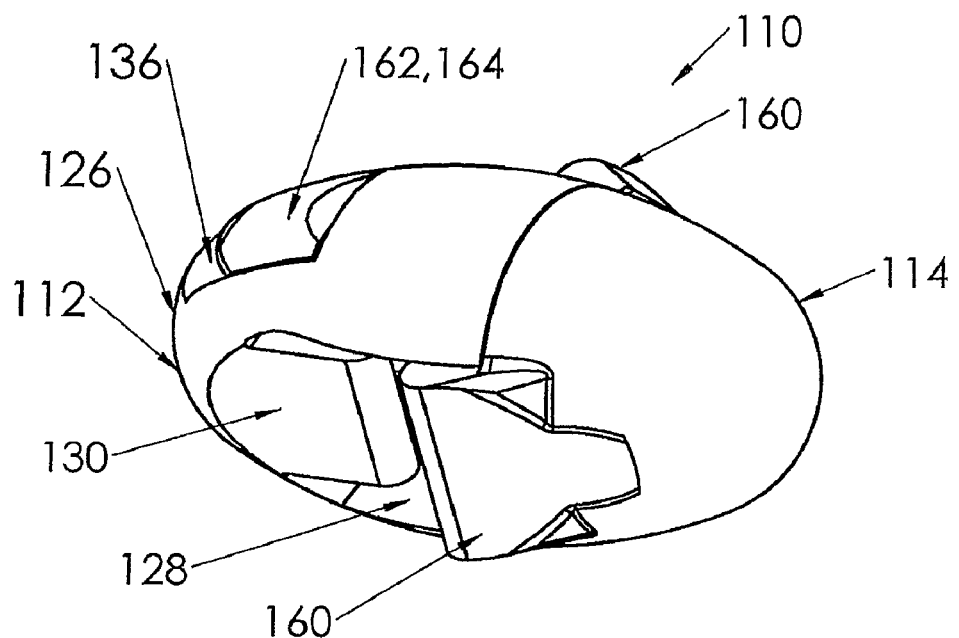
Figure 15:
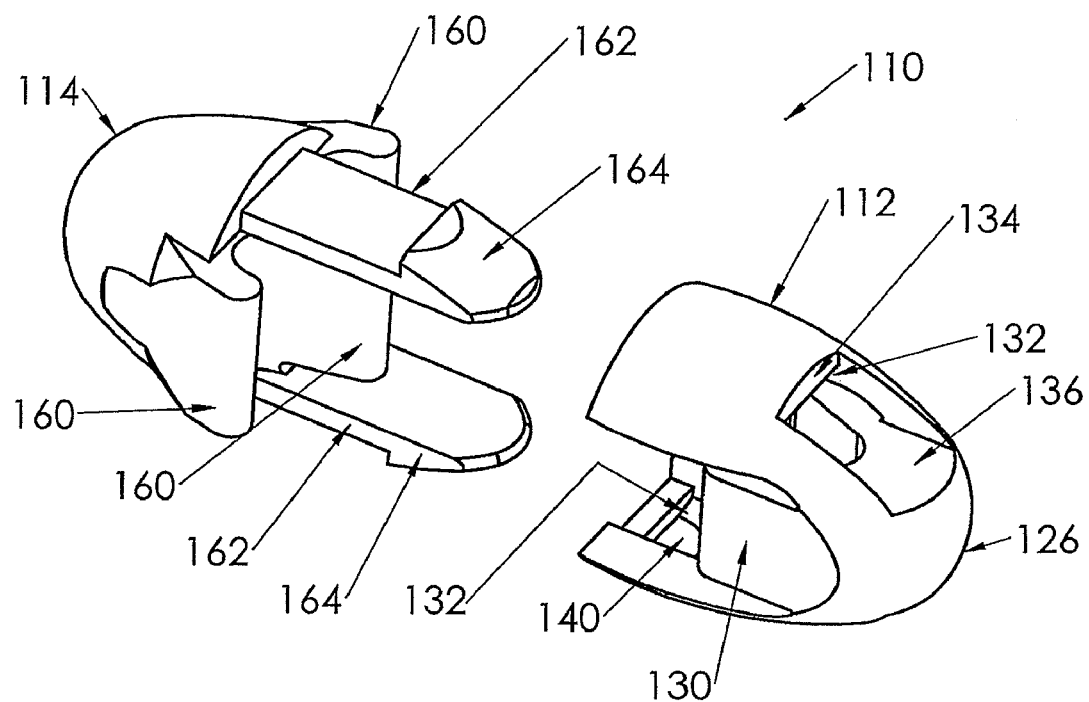
FIG. 15 is an exploded isometric view similar to FIG. 13.
Figure 16:
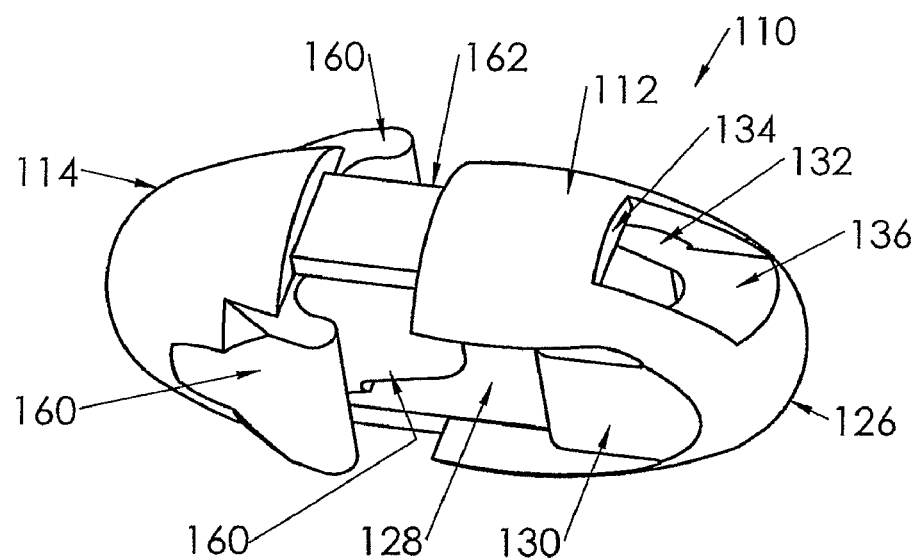
FIG. 16 is an isometric view of the two clamp portions of FIG. 15 assembled together in a nonclamping state.

Certain terminology is used herein for convenience only and is not to be taken as a limitation on the present invention. The embodiments illustrated below are not intended to be exhaustive or to limit the invention to the precise form disclosed, but are chosen and described to best explain the principle of the invention and its application and practical use and to enable others skilled in the art to best utilize the invention. FIGS. 1 to 11 illustrate a first embodiment of clamp assembly of the present invention, FIG. 12 illustrates a second embodiment, and FIGS. 13 to 20 illustrate a third embodiment.

Clamp assembly 10 of FIGS. 1 to 11 includes two pieces, a housing 12 and a clamp 14. Housing 12 has two side walls 20,22 extending from first end 24 to second end 26, and each side wall includes an opening such that the openings are aligned to define a tubing-receiving channel 28 for flexible tubing 100 having a lumen 102 for fluid flow, shown in FIG. 1. Clamp 14 is slidable within the housing 12 in a transverse direction, that is, in a direction perpendicular to the channel and the flexible tubing 100, and between a first position and a second position.

Figure 1:
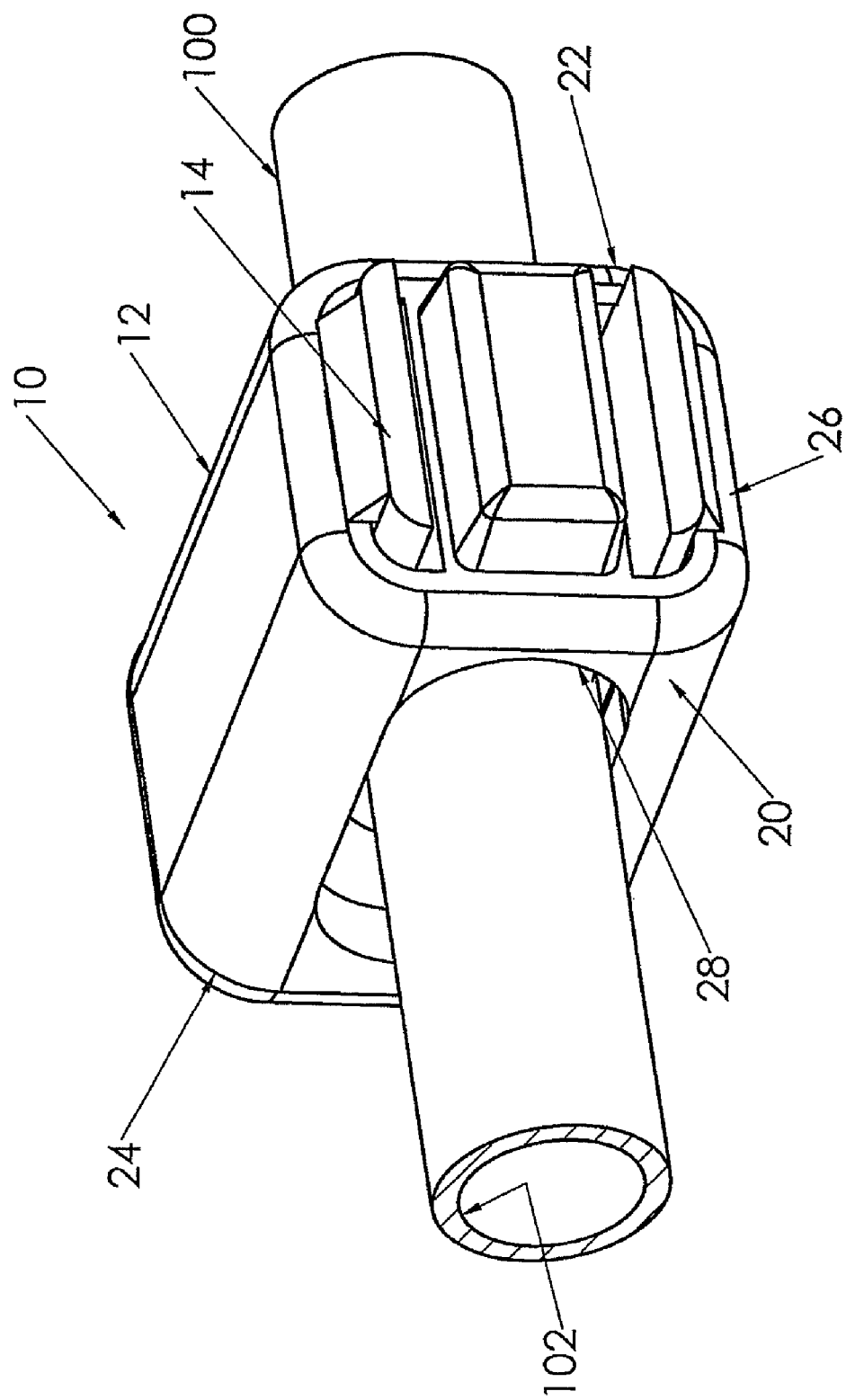
FIG. 1 is an isometric view of the clamp assembly of the present invention shown in its closed state with a length of flexible tubing extending therethrough.
Figure 2:
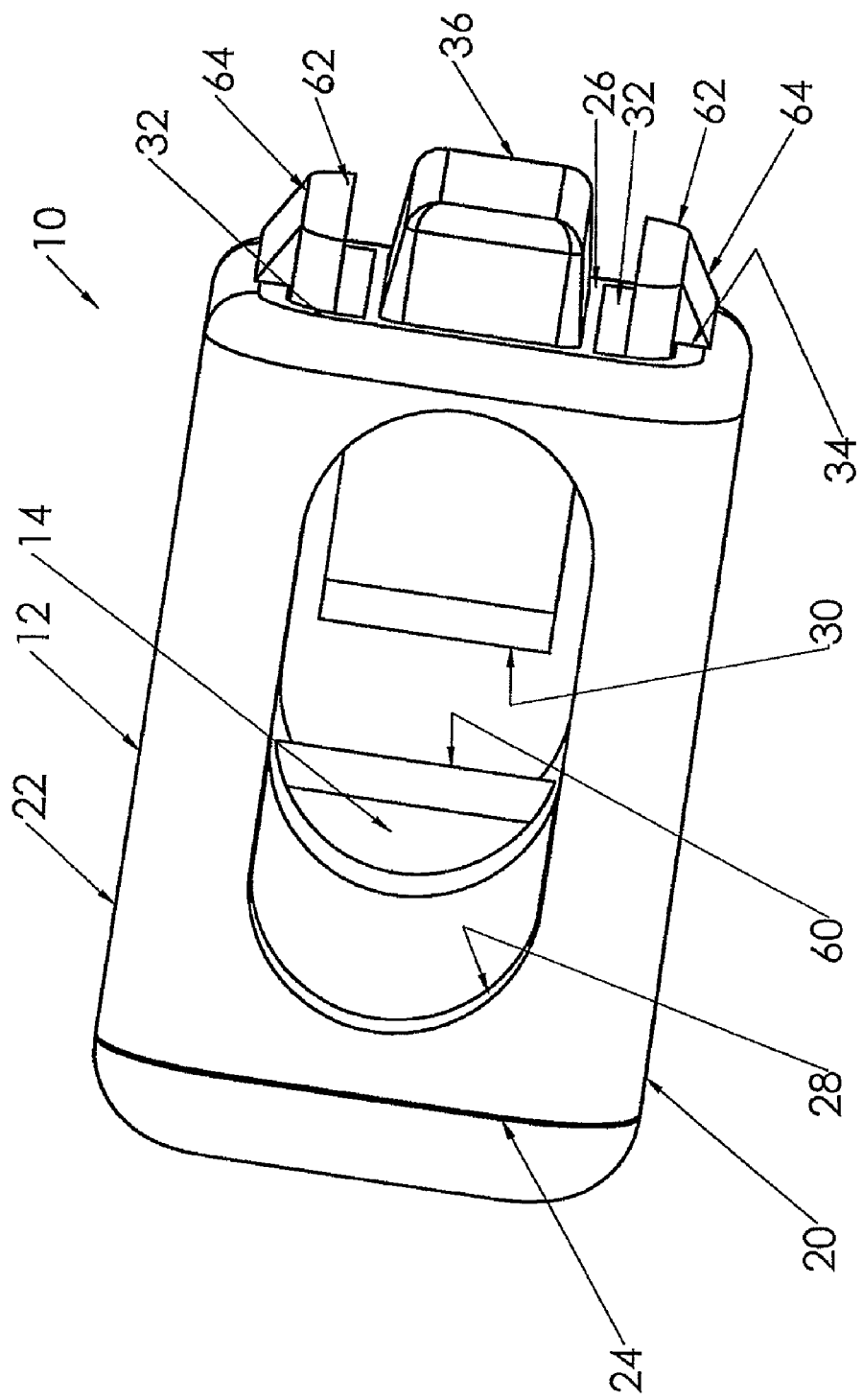
FIG. 2 is another isometric view of the clamp assembly of FIG. 1 without the tubing and illustrating the tubing channel therethrough and the tubing-engaging ribs of the housing and the clamp.
Figure 3:
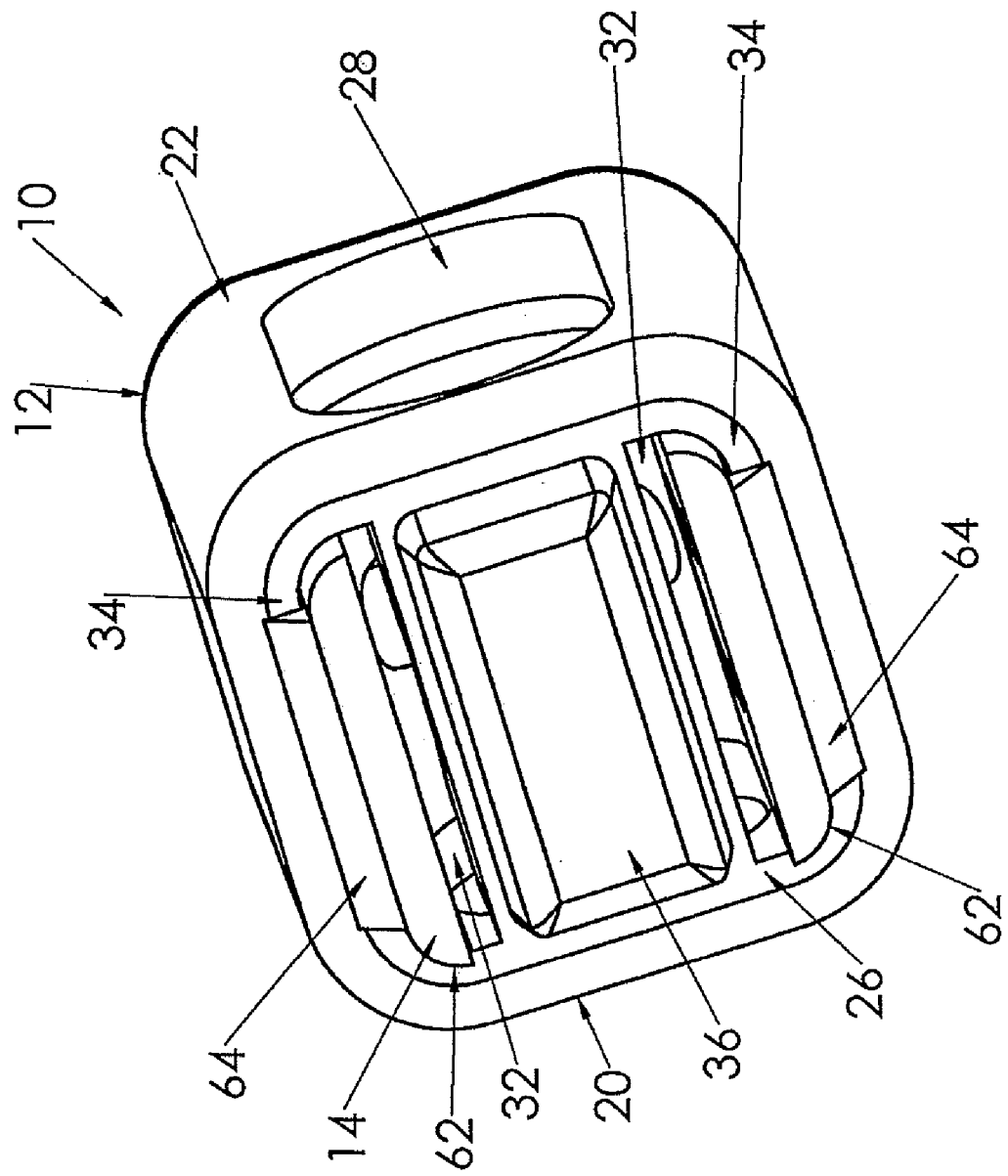
FIG. 3 is an isometric end view of the clamp assembly of FIG. 2.
Figure 4:
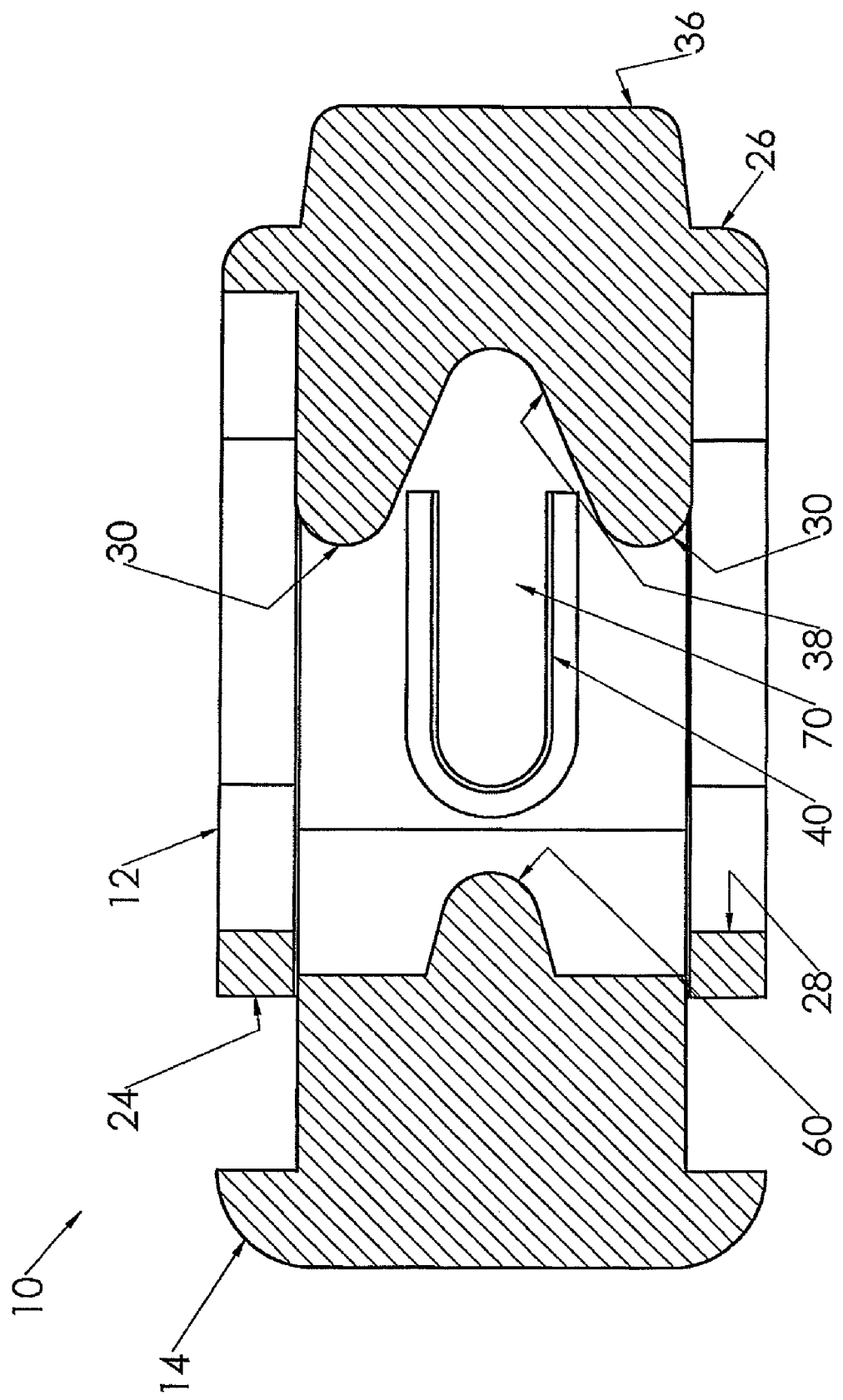
FIGS. 4 and 5 are cross-section views showing the clamp in its first position and its second position, respectively.
Figure 5:
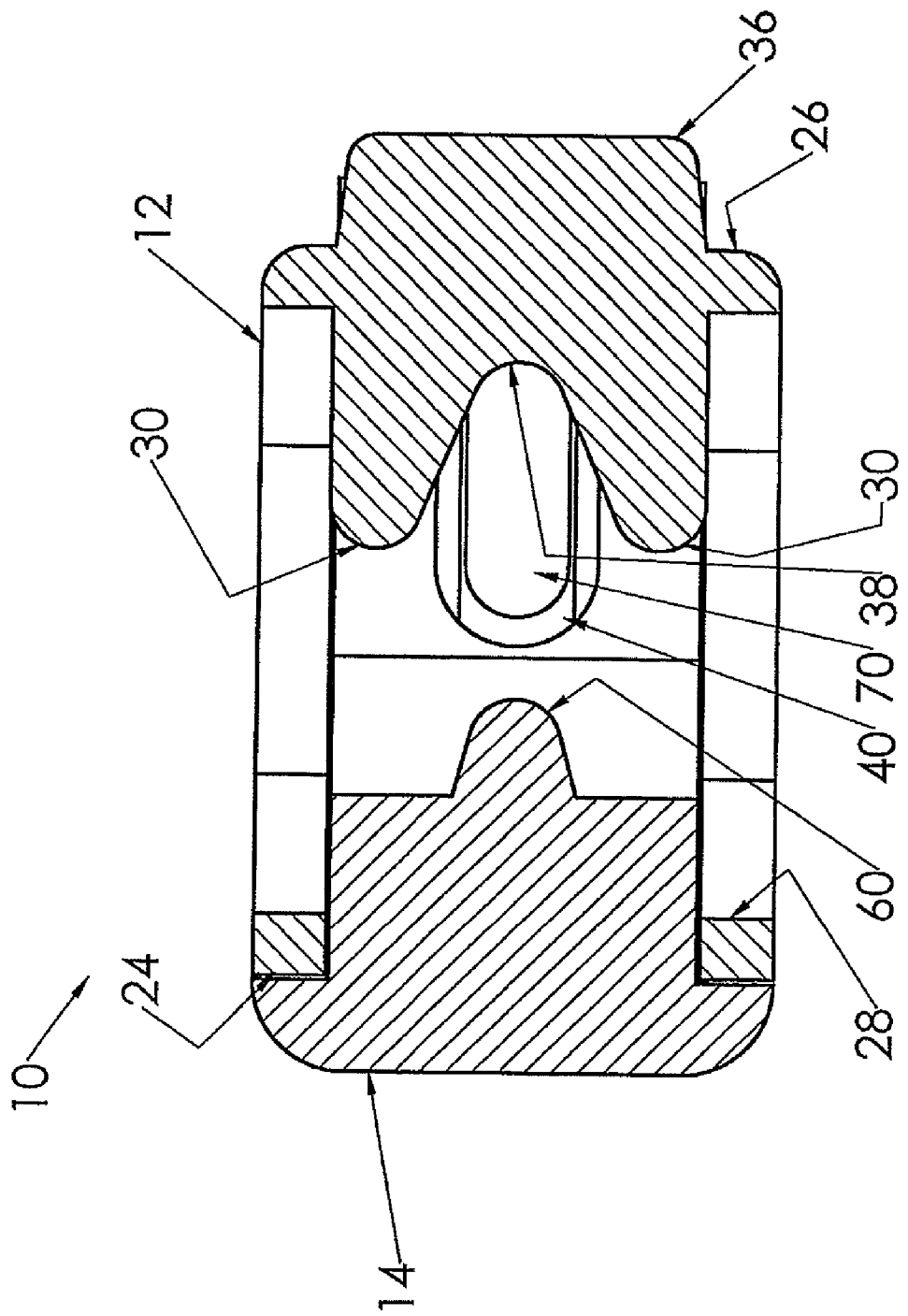

At least one of the clamp 14 and the housing 12 includes at least one tubing-engaging rib extending at least to the channel through which the tubing 100 will extend upon mounting of the assembly 10 to the tubing so that the at least one rib (or jaw) engages and compresses the tubing against an opposing surface of the other of the clamp and the housing, upon movement of the clamp 14 to its second position, thus occluding the tubing. In FIG. 2, it is seen that clamp 14 includes at least one such tubing-engaging rib 60, and housing 12 includes at least one tubing-engaging rib 30. In FIGS. 4 and 5, it is seen that clamp 14 has one such tubing-engaging rib 60 and housing 12 includes two such tubing-engaging ribs 30, each offset from rib 60 in a direction parallel to the channel and thus to tubing 100. Upon movement of the clamp to its second position, flexible tubing 100 would be forced to assume a tortuous path and its side walls are forced together along the length of the tubing-receiving channel 28, whereby the tubing becomes occluded.

Figure 6:
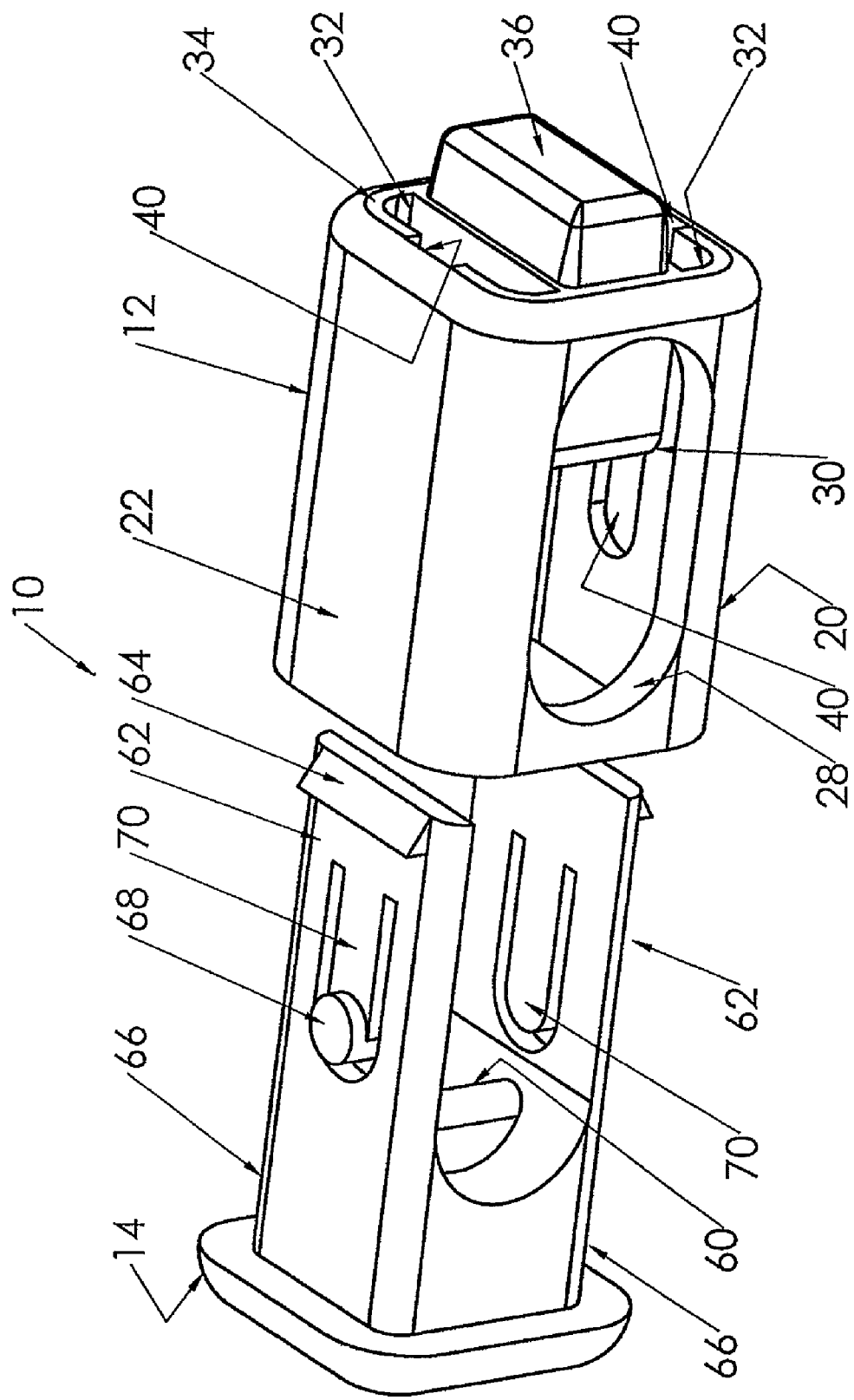
FIGS. 6 and 7 are an exploded isometric view and an elevation view, respectively, of the clamp assembly of the present invention.
Figure 7:
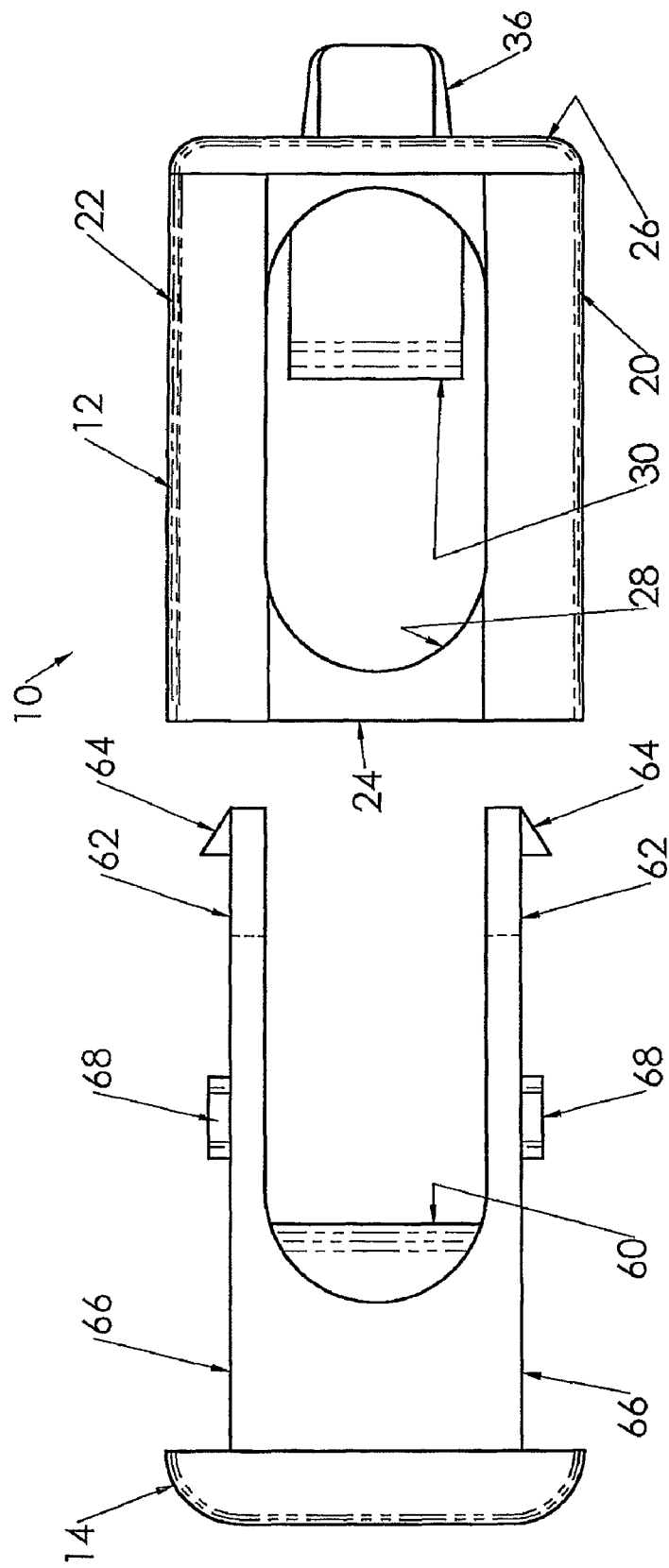
Figure 8:
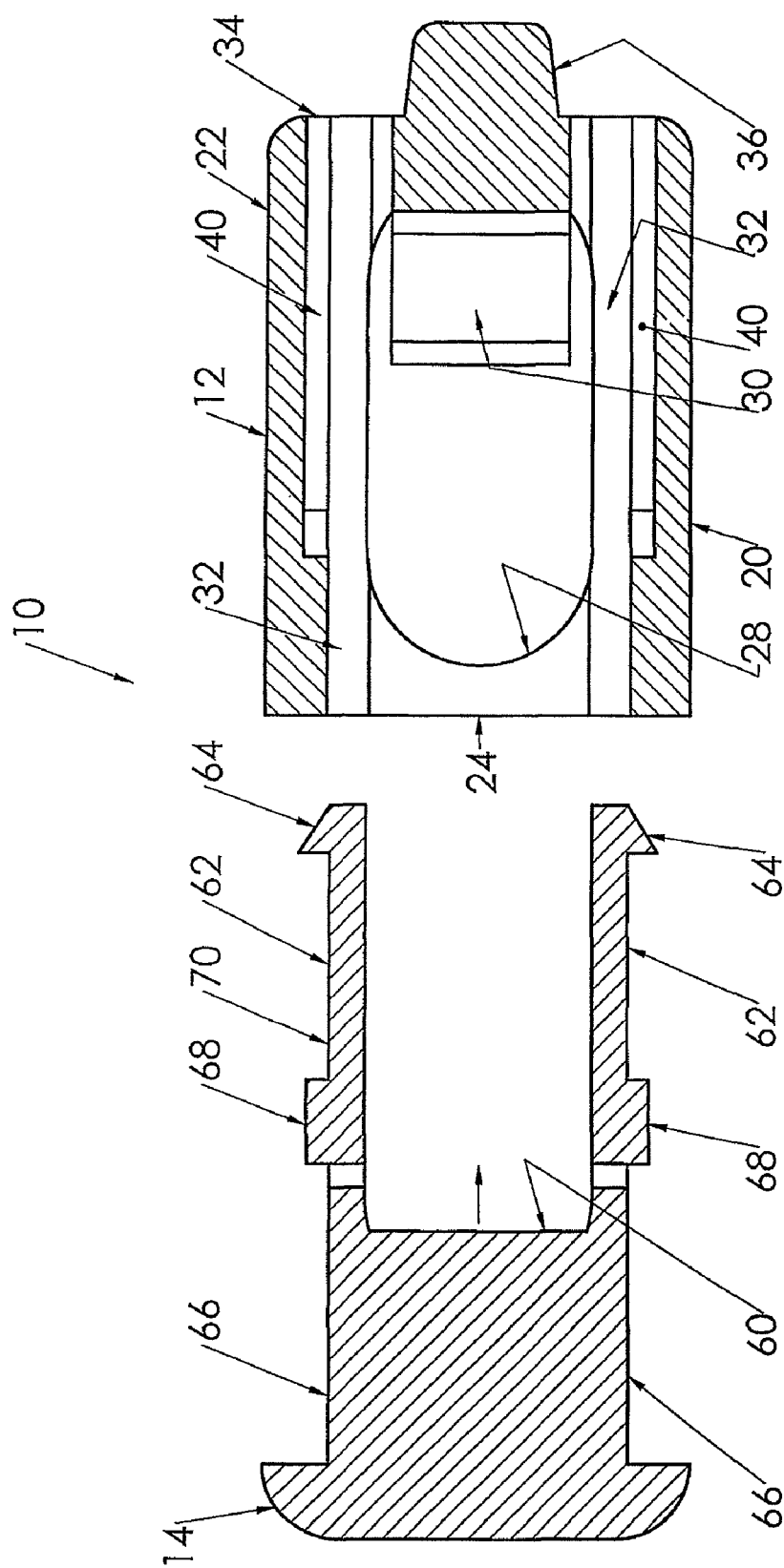
FIGS. 8 to 10 are cross-section views of the clamp assembly with the clamp in its first position, an intermediate position, and its second position, respectively.
Figure 9:
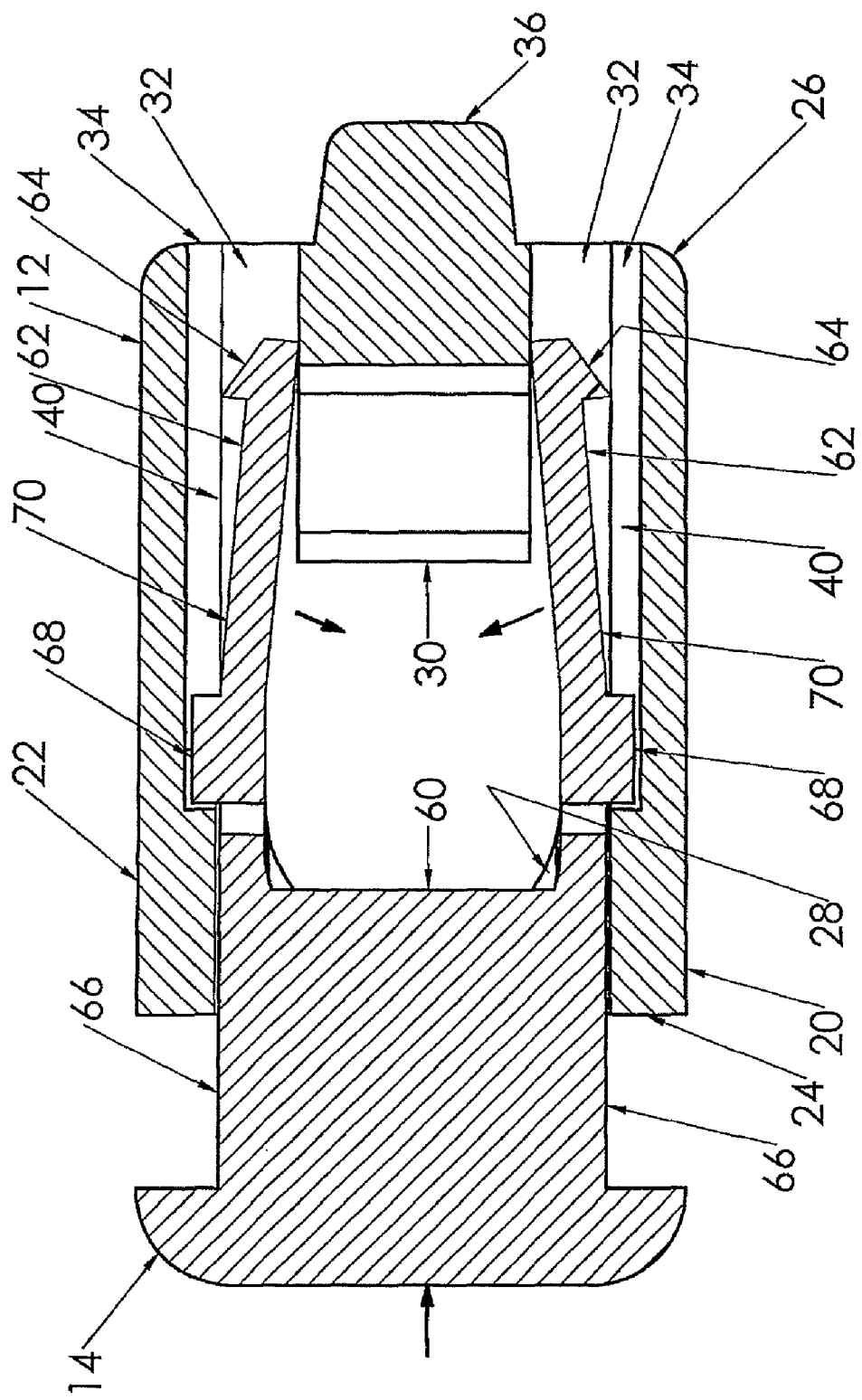
Figure 10:
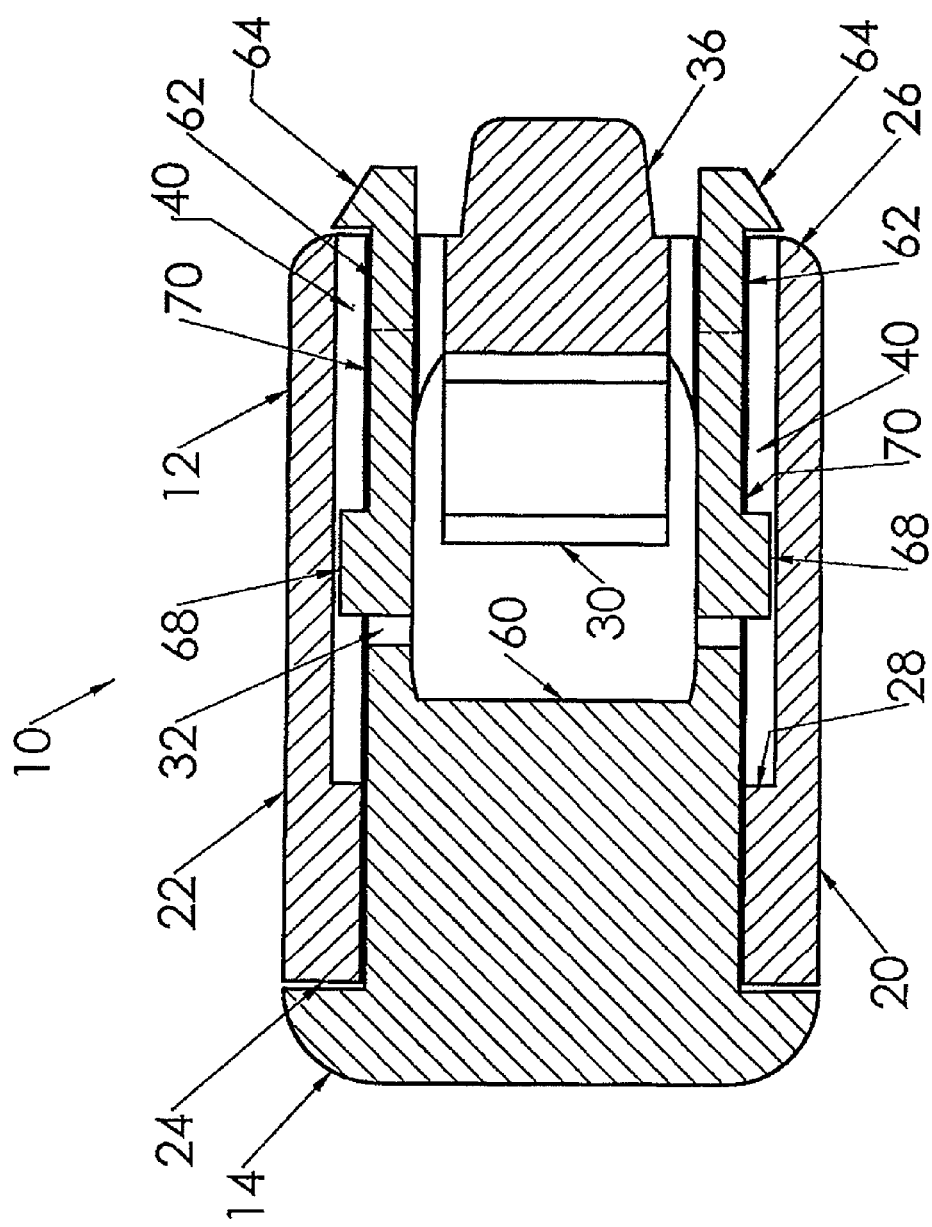
Figure 11:
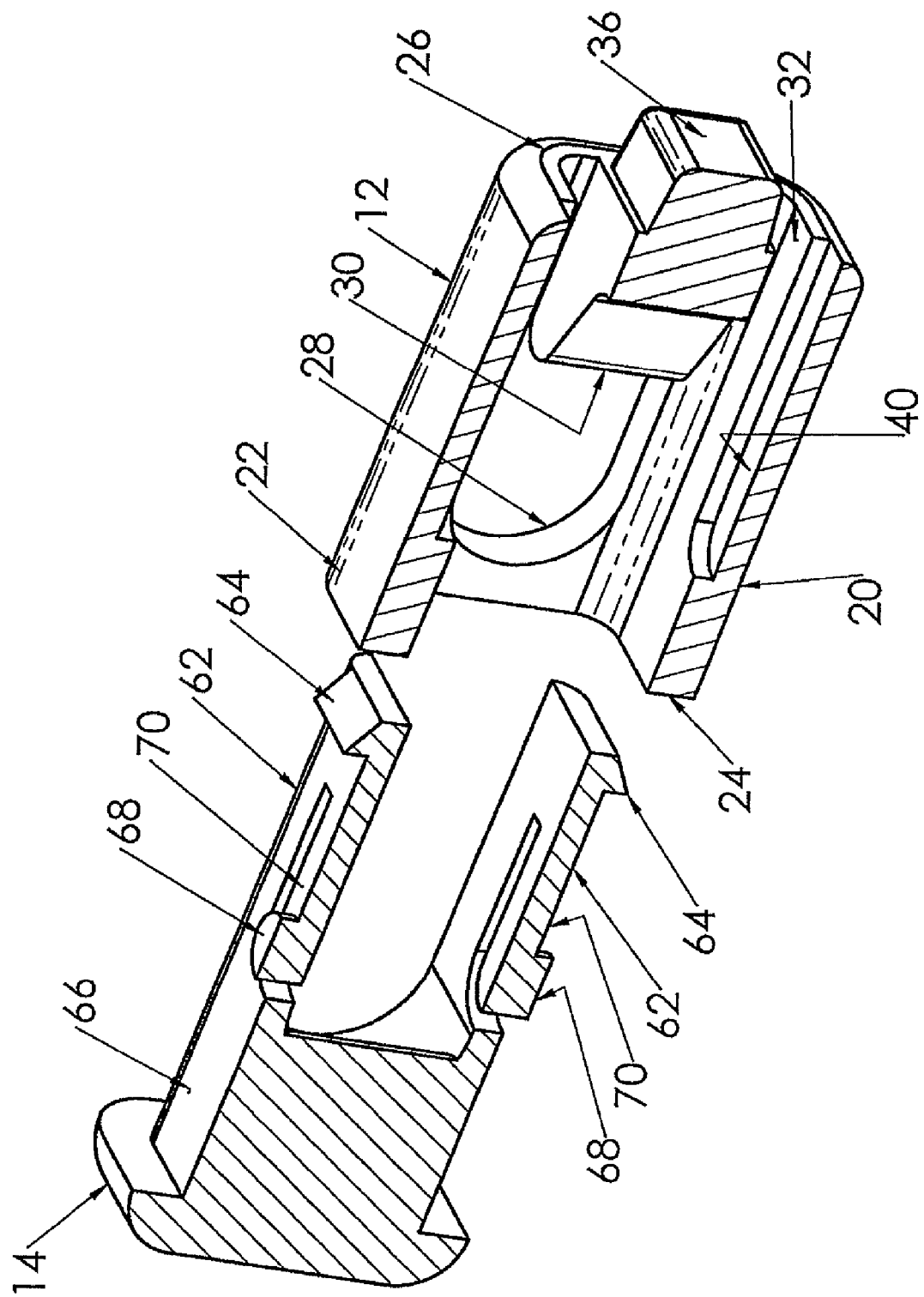
FIG. 11 is an exploded isometric cross-section view of the clamp assembly.

Referring to FIGS. 2 and 6, clamp 14 is shown to include a pair of latch arms 62 extending to free ends 64 from respective opposed side walls 66 of the clamp, in a direction transverse to the tubing-receiving channel 28; the pair of latch arms provide mutual redundancy, since both must be delatched to permit parting movement of the clamp. The latch arms 62 extend through corresponding channels 32 of housing 12 and, preferably, beyond the latch arm channel exits at second housing end 26 for latch projections of latch arm free ends 64 to latchingly engage surfaces 34 of second housing end 26 adjacent the channel exits, which act as catches when clamp 14 is in its second, occluding position.

It is also seen that free ends 64 are exposed to be manually deflectable toward each other to delatch the latch arms 62 when desired, to return clamp 14 to its first, or open, position primarily by pressure from the occluded tubing tending to resume its original cylindrical shape. Second end 26 of housing 12 is seen to have a boss 36 projecting outwardly between the channel exits to provide protection against inadvertent engagement with latch arm free ends 64 and possible unintentional and undesirable delatching thereof. As is easily discerned, latch arms 62 are deflectable inwardly, and any engagement by the flexible tubing within the channel especially when occluded simply urges the latch arms against the housing side walls and has no tendency to delatch the latch arm free ends from their latching engagement with the housing.

In FIGS. 4 and 5 are illustrated the first and second positions of the clamp 14 with respect to housing 12. Tubing-engaging rib 60 of clamp 14 is seen to be aligned with a groove 38 between tubing-engaging ribs 30 of housing 12. In the second, occluding position, it is seen that flexible tubing would assume a tortuous path sufficient to occlude fluid flow therethrough.

Seen best in FIGS. 6 to 11 are detents 68 of clamp 14 provided at free ends of spring arms 70 defined into latch arms 62 spaced from latch arm free ends 64. Upon assembly of clamp 14 in housing 12, detents 68 become seated in recesses 40 defined into interior surfaces of opposed side walls 20,22 of housing 12, with recesses 40 in communication with channels 32 and extending to second end 26 of housing 12 for detents 68 to travel therein as clamp 14 is moved between its first and second positions.

FIG. 12 illustrates an alternate embodiment of housing 12' in which the top and bottom housing walls 42',44' define recesses or slots 40' spaced from the second end 26' into which the free ends of the clamp latch arms (see FIG. 6) will snap when the clamp is in its first or open position, eliminating the need for detents and detent recesses.

A second embodiment of clamp 110 is depicted in FIGS. 13 to 20, generally having an oblate or ovate or ovoid shape which is atraumatic to the patient and minimizing snagging risk. Clamp 110 includes first 112 and second 114 clamp portions, each defining a portion of the channel through which tubing 100 will extend. Unlike clamp 10 of FIGS. 1 to 11, clamp 110 is applied to the tubing from laterally thereof, eliminating the need for threading a tubing end through a clamp housing, and permitting removal from the tubing, if desired. Similarly to clamp 10, however, clamp 110 when assembled has a first position or state in which the tubing is not clamped or occluded by the clamp (see FIGS. 16 and 19), and a second position or state in which the tubing is clamped and occluded by the clamp (see FIGS. 13, 14, 18 and 20).

Figure 17:
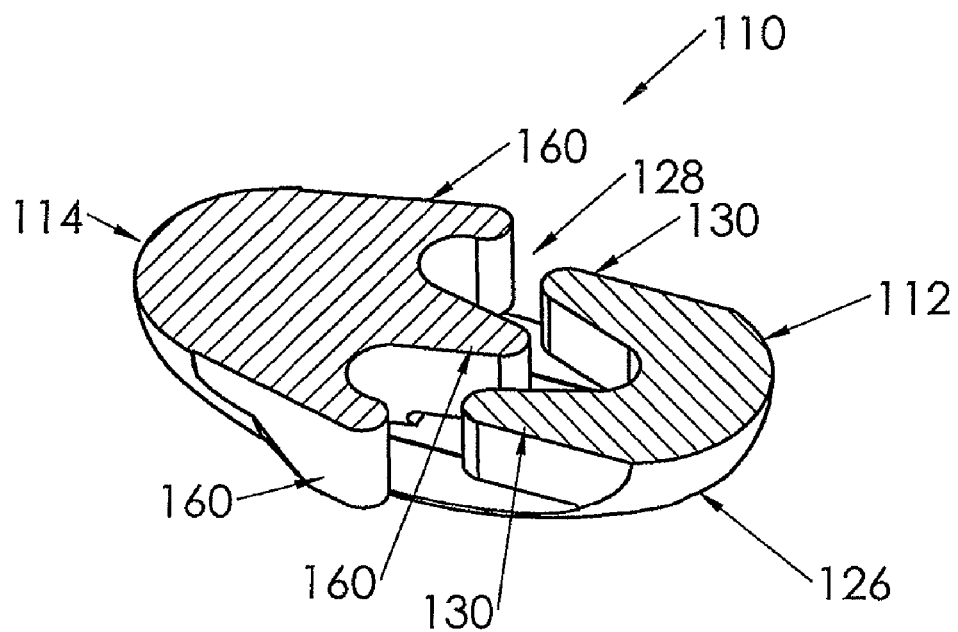
FIG. 17 is a cross-section view of the two clamp portions of FIGS. 13 to 16 in a clamping state illustrating the clamping surfaces engageable with a flexible conduit therebetween and occluded thereby.
Figure 18:
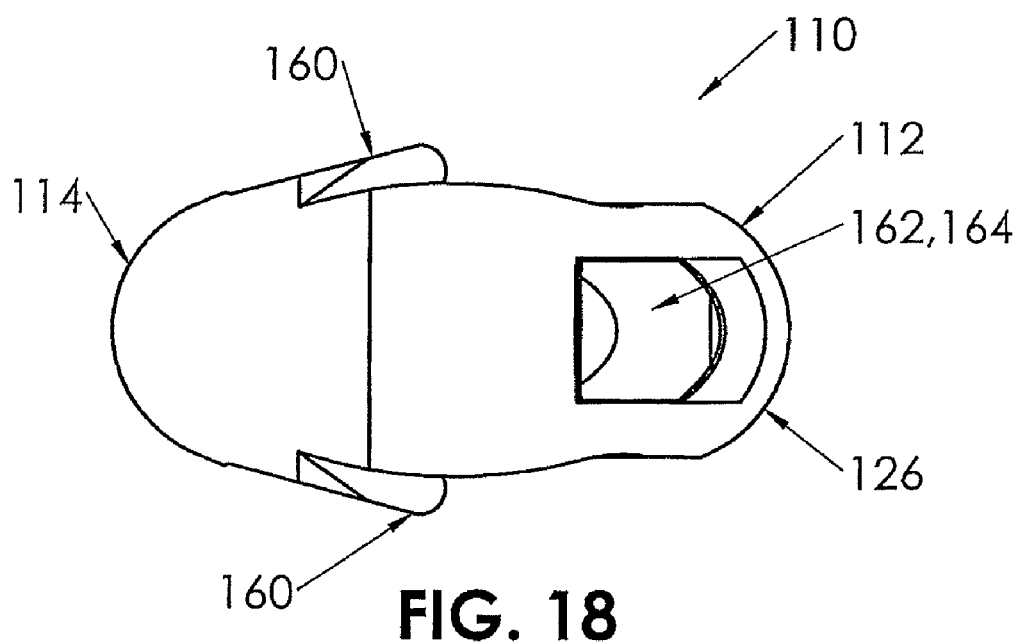
FIG. 18 is a plan view of the clamp assembly of FIGS. 13 and 14.

First clamp portion 112 is shown to include two tubing-engaging ribs 130, while second clamp portion 114 includes three tubing-engaging ribs 160 which are offset from tubing-engaging ribs 130 to define a tortuous path or channel 128 for the flexible tubing, as demonstrated in FIG. 17. Such a tortuous tubing channel 128 with a properly selected transverse spacing of the five tubing-engaging ribs, and a properly selected narrow distance between the clamp portions 112,114 when in the second, occluding state, assure occlusion of the flexible tubing 100.

Figure 19:
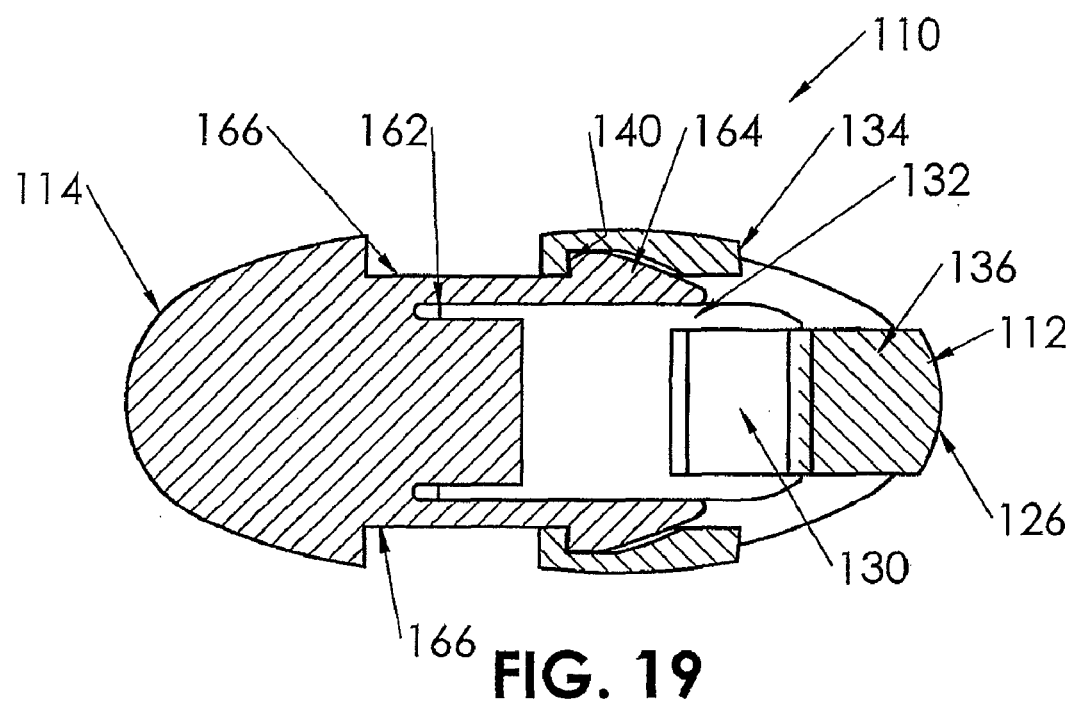
FIGS. 19 and 20 are cross-sectional views of the clamp assembly of FIGS. 13 to 18 in an unclamping state and a clamping state, respectively.
Figure 20:
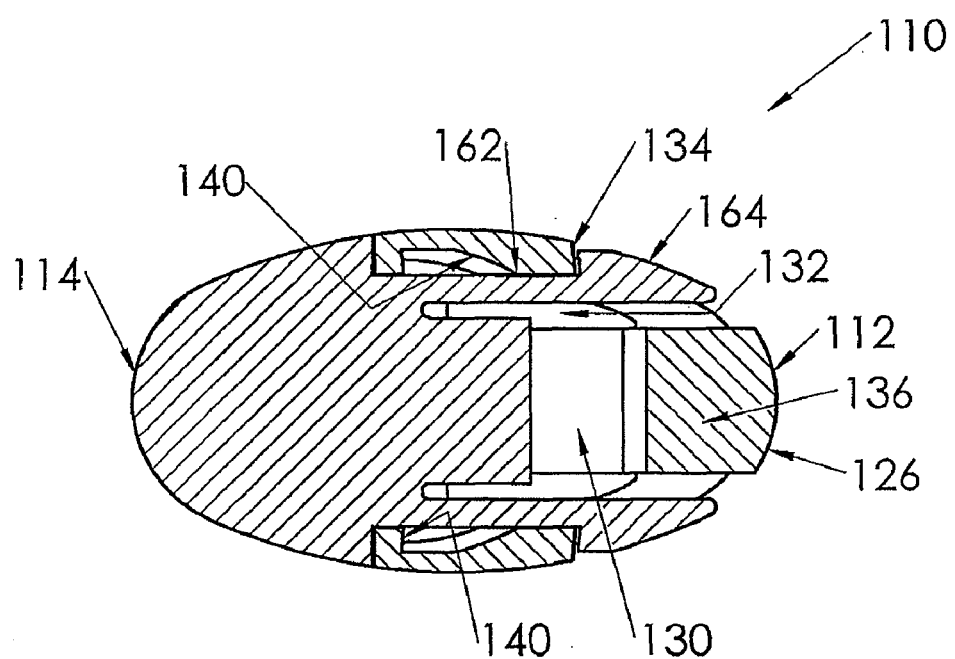

As with clamp 14 of FIGS. 1 to 11, second clamp portion 114 includes a pair of latch arms 162 extending to free ends 164 from respective opposed side walls 166 of second clamp portion 114, in a direction transverse to the tubing channel; the pair of latch arms provide mutual redundancy, since both must be delatched to permit movement of the clamp 110. As best shown in FIGS. 19 and 20, the latch arms 162 extend through corresponding channels 132 of clamp portion 12 and, preferably, beyond the channel exits at first clamp portion end 126 for latch projections of free ends 164 to latchingly engage surfaces 134 of clamp portion end 126, which act as catches when second clamp portion 114 is in its second, occluding position. Referring to FIG. 19, and similarly to housing 12' of FIG. 12, first clamp portion 112 includes a pair of recesses or slots 140 along channels 132 spaced from end 126 into which the free ends of the latch arms 162 will snap when the clamp assembly is in its first or unclamped position.

It is also seen that, when clamp 110 is in its second or occluding position, free ends 164 of latch arms 162 are exposed to be manually deflectable toward each other to delatch the latch arms 162 when desired, to return clamp assembly 110 to its first, or unclamping, position primarily by pressure from the occluded tubing tending to resume its original cylindrical shape. First clamp portion end 126 is seen to have a boss 136 projecting outwardly between the channel exits to provide protection against inadvertent engagement with latch arm free ends 164 and possible unintentional and undesirable delatching thereof. As is easily discerned, latch arms 162 are deflectable inwardly or toward each other, and any engagement by the flexible tubing within the tubing channel especially when occluded simply urges the latch arms against the clamp portion side walls and has no tendency to delatch the latch arm free ends from their latching engagement with first clamp portion 112.

Clamp assembly 10,110 can have a dimension parallel to the flexible tubing 100 extending therethrough, of less than one-half of an inch, or under 127 mm, and is structurally robust and durable over many actuation cycles, with great resistance to inadvertent delatching. The clamp and the housing may be molded of polyethylene plastic, or of polypropylene, or other suitable materials.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:

1. A clamp assembly for flexible tubing, comprising:

first and second clamp portions, each having first and second ends, associated with and self-securable to each other to define a tubing-receiving channel therebetween for a length of flexible tubing to be received thereinto, the first and second clamp portions axially moveable relative to one another in a direction transverse to the tubing-receiving channel between a first position in which the length of flexible tubing is substantially unengaged while extending through the assembly of the first and second clamp portions, and a second position, whereby the first and second clamp portions compress and occlude the flexible tubing therebetween when in the second position, wherein one of the first and second clamp portions include at least one tubing-engaging rib for engaging and pressing the flexible tubing against an impingement surface of the other of the first and second clamp portions when the first and second clamp portions are in the second position sufficiently to occlude the flexible tubing and wherein the second clamp portion includes a pair of detents that cooperate with a corresponding pair of recesses of the first clamp portion to secure together the clamp assembly when in the first position, each detent is defined on a free end of a spring arm defined on a respective latch arm of the second clamp portion spaced from the free end thereof wherein the spring arm is deflectable inwardly during assembly of the first and second clamp portions by one of the opposing side walls of the first clamp portion.

2. The clamp assembly of claim 1, wherein the shape of the first and second clamp portions when in the second position, is generally oblong.

3. The clamp assembly of claim 1, wherein the first clamp portion is a housing having a first end and a second end, a pair of opposing side walls joining the first and second ends, and the tubing-receiving channel extends through openings in respective ones of the opposing side walls of the housing.

4. The clamp assembly of claim 3, wherein the openings in the opposing side walls of the first clamp portion are oblong such that the tubing is translatable therewithin transversely with respect thereto when the second clamp portion is moved between the first and second positions with respect to the first clamp portion.

5. A clamp assembly for flexible tubing, comprising:

first and second clamp portions, each having first and second ends, associated with and self-securable to each other to define a tubing-receiving channel therebetween for a length of flexible tubing to be received thereinto, the first and second clamp portions being affixable to each other to define a first position in which the length of flexible tubing is substantially unengaged while extending through the assembly of the first and second clamp portions, and a second position, whereby the first and second clamp portions compress and occlude the flexible tubing therebetween when in the second position, wherein one of the first and second clamp portions include at least one tubing-engaging rib for engaging and pressing the flexible tubing against an impingement surface of the other of the first and second clamp portions when the first and second clamp portions are in the second position sufficiently to occlude the flexible tubing, and wherein the second clamp portion has a pair of detents and the first clamp portion has a pair of recesses associated with respective ones of the detents and the recesses are shallow grooves defined into inside surfaces of the opposing side walls of the first clamp portion extending in a direction between the first and second ends thereof.

6. A clamp assembly for flexible tubing, comprising:
first and second clamp portions, each having first and second ends, associated with and self-securable to each other to define a tubing-receiving channel therebetween for a length of flexible tubing to be received thereinto, the first and second clamp portions being affixable to each other to define a first position in which the length of flexible tubing is substantially unengaged while extending through the assembly of the first and second clamp portions, and a second position, whereby the first and second clamp portions compress and occlude the flexible tubing therebetween when in the second position,
wherein one of the first and second clamp portions include at least one tubing-engaging rib for engaging and pressing the flexible tubing against an impingement surface of the other of the first and second clamp portions when the first and second clamp portions are in the second position sufficiently to occlude the flexible tubing, and wherein the impingement surface of the other of the first and second clamp portions is defined by at least one tubing-engaging rib to assist in occluding the flexible tubing when the clamp assembly is in the second position.

7. The clamp assembly of claim 6, wherein the impingement surface is defined by two tubing-engaging ribs of the one of the first and second clamp portions that extend to either side of the at least one tubing-engaging rib of the other thereof such that all of the tubing-engaging ribs cause the flexible tubing to be deformed into a tortuous path when the clamp assembly is in the second position, occluding the tubing.

8. The clamp assembly of claim 6, wherein each tubing-engaging rib concludes in a rounded tubing-engaging surface.

9. A clamp assembly for flexible tubing, comprising:
first and second clamp portions, each having first and second ends, associated with and self-securable to each other to define a tubing-receiving channel therebetween for a length of flexible tubing to be received thereinto, the first and second clamp portions being affixable to each other to define a first position in which the length of flexible tubing is substantially unengaged while extending through the assembly of the first and second clamp portions, and a second position, whereby the first and second clamp portions compress and occlude the flexible tubing therebetween when in the second position,
wherein one of the first and second clamp portions include at least one tubing-engaging rib for engaging and pressing the flexible tubing against an impingement surface of the other of the first and second clamp portions when the first and second clamp portions are in the second position sufficiently to occlude the flexible tubing, and wherein the one of the first and second clamp portions includes a pair of outer tubing-engaging ribs offset along the tubing-receiving channel from the at least one tubing-engaging rib to extend along outer sides of respective ones of the pair of tubing-engaging ribs of the other of the first and second clamp portions.

10. The clamp assembly of claim 9, wherein the outer tubing-engaging ribs extend in respective diverging directions with respect to the direction in which the at least one tubing-engaging rib extends.

11. A clamp assembly for flexible tubing, comprising:
first and second clamp portions, each having first and second ends, associated with and self-securable to each other to define a tubing-receiving channel therebetween for a length of flexible tubing to be received thereinto, the first and second clamp portions being affixable to each other to define a first position in which the length of flexible tubing is substantially unengaged while extending through the assembly of the first and second clamp portions, and a second position, whereby the first and second clamp portions compress and occlude the flexible tubing therebetween when in the second position,
wherein one of the first and second clamp portions include at least one tubing-engaging rib for engaging and pressing the flexible tubing against an impingement surface of the other of the first and second clamp portions when the first and second clamp portions are in the second position sufficiently to occlude the flexible tubing, and wherein the impingement surface of one of the first and second clamp portions is defined by two tubing-engaging ribs, and the impingement surface of the other thereof is defined by three tubing-engaging ribs offset along the tubing channel from the two tubing-engaging ribs, such that all of the tubing-engaging ribs cause the flexible tubing to be deformed into a tortuous path when the clamp assembly is in the second position, occluding the tubing.

12. A clamp assembly for flexible tubing, comprising:
first and second clamp portions, each having first and second ends, associated with and self-securable to each other to define a tubing-receiving channel therebetween for a length of flexible tubing to be received thereinto, the first and second clamp portions axially moveable relative to one another in a direction transverse to the tubing-receiving channel between a first position in which the length of flexible tubing is substantially unengaged while extending through the assembly of the first and second clamp portions, and a second position, whereby the first and second clamp portions compress and occlude the flexible tubing therebetween when in the second position,
wherein one of the first and second clamp portions include at least one tubing-engaging rib for engaging and pressing the flexible tubing against an impingement surface of the other of the first and second clamp portions when the first and second clamp portions are in the second position sufficiently to occlude the flexible tubing and
wherein the second clamp portion includes at least one latch arm projecting longitudinally from the second end thereof and having a free end that latchingly engages a catch of the first clamp portion when in the second position, wherein each at least one latch arm is deflectable in a direction generally perpendicular to the direction of movement of the first and second clamp portions.

13. The clamp assembly of claim 12, wherein the at least one latch arm extends within one of opposing side walls of the first clamp portion and the catch is provided at the second end thereof.

14. The clamp assembly of claim 13, wherein the second clamp portion has two latch arms extending from respective opposing sides thereof and that extend on opposed sides of the tubing-receiving channel through the first clamp portion, which has respective catches associated with the two latch arms.

15. The clamp assembly of claim 14, wherein the latch arm free ends project through latch arm channels of the first clamp portion and beyond the second end thereof to engage the respective catches, and are exposed to be manually engaged to unlatch the latch arms.

16. The clamp assembly of claim 15, wherein the first clamp portion includes a boss between the latch arm channels projecting a distance from the second end at least equal to the distance that the free ends of the latch arms of the second clamp portion extend when in the second position.

17. The clamp assembly of claim 15, wherein the first clamp portion includes a pair of recesses into top and bottom surfaces spaced from the second end thereof into which free ends of the latch arms of the second clamp portion snap when the clamp assembly is in its first position.

\* \* \* \* \*